(12) United States Patent
Chen et al.

(10) Patent No.: US 8,833,143 B2
(45) Date of Patent: Sep. 16, 2014

(54) HYDRAULIC ACCUMULATOR PRE-CHARGE PRESSURE DETECTION

(75) Inventors: Dayao Chen, Bolingbrook, IL (US);
Pengfei Ma, Naperville, IL (US);
Tonglin Shang, Bolingbrook, IL (US);
Bryan J. Hillman, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 355 days.

(21) Appl. No.: 13/427,072

(22) Filed: Mar. 22, 2012

(65) Prior Publication Data

US 2013/0247999 A1    Sep. 26, 2013

(51) Int. Cl.
*G01M 3/02*       (2006.01)
*G01N 3/32*       (2006.01)

(52) U.S. Cl.
CPC .. *G01N 3/32* (2013.01); *G01M 3/02* (2013.01)
USPC ............................................................ 73/37

(58) Field of Classification Search
CPC ....... G01N 3/32; G01N 15/0826; G01M 3/02; A61B 19/46
USPC ............................................................ 73/37
See application file for complete search history.

(56) References Cited

U.S. PATENT DOCUMENTS

| | | | |
|---|---|---|---|
| 3,494,192 A | 2/1970 | Abduz | |
| 3,662,333 A * | 5/1972 | Howard et al. | ............... 340/452 |
| 4,781,061 A | 11/1988 | Baumgartl | |
| 5,221,125 A | 6/1993 | Okochi et al. | |
| 5,779,327 A | 7/1998 | Nakashima et al. | |
| 6,702,401 B2 | 3/2004 | Sherriff | |
| 6,758,096 B1 | 7/2004 | Schon et al. | |
| 2011/0046901 A1 | 2/2011 | Boissonneau et al. | |
| 2011/0264339 A1 | 10/2011 | Wang et al. | |
| 2013/0253854 A1* | 9/2013 | Chen et al. | ............... 702/50 |

FOREIGN PATENT DOCUMENTS

| | | |
|---|---|---|
| DE | 10 2005 052 640 | 2/2007 |
| DE | 102005052640 | 2/2007 |
| JP | 06052211 | 7/1994 |
| JP | 07139501 | 5/1995 |
| JP | 2001013044 | 1/2001 |
| JP | 2004156943 | 6/2004 |

* cited by examiner

*Primary Examiner* — Hezron E Williams
*Assistant Examiner* — Rodney T Frank
(74) *Attorney, Agent, or Firm* — M. Daniel Spillman (57) ABSTRACT

A system including a hydraulic accumulator, a pressure sensor, a fluid source and a data processor to detect a pre-charge pressure is provided. The hydraulic accumulator includes first and second fluid chambers and a separator therebetween. The hydraulic accumulator has an associated pre-charge pressure. The pressure sensor is connected to the first fluid chamber. The data processor is connected to the pressure sensor. The data processor is configured to determine a first and second rate of pressure changes, and a transition pressure between the first and second rates. The approximate pre-charge pressure is determined based on the transition pressure.

20 Claims, 7 Drawing Sheets

HYDRAULIC ACCUMULATOR PRE-CHARGE PRESSURE DETECTION

TECHNICAL FIELD

The present disclosure relates to hydraulic accumulators and more particularly to determining pre-charge pressure of the hydraulic accumulator.

BACKGROUND

Pre-charge pressure of a hydraulic accumulator needs to be periodically checked after installation in a hydraulic system to ensure operational health of the accumulator. Typical solutions for detecting the accumulator health involve connecting a gas pressure gauge and/or a modular kit to a gas valve of the hydraulic accumulator, when the machine is stopped and the fluid in the hydraulic accumulator is not pressurized. The gas pressure gauge provides a reading of the pre-charge pressure. Depending on such readings, the hydraulic accumulator is either re-charged or completely overhauled or replaced. Hence, typical solutions required physically connecting the hydraulic accumulator to the pressure gauge. However, the accumulator can be located on a machine such that it is difficult to access and couple the gas pressure gauge.

In one example, German Patent Number DE102005052640 relates to a method involving determination of a difference in accumulator volume using a flow regulator with constant adjustable flow rate and an actuating valve with preset response time. The method also involves determination of pressure values before and after the fluid withdrawal from a hydraulic accumulator using a pressure sensor based on its recalled calculated accumulator volume at an empty state.

SUMMARY OF THE DISCLOSURE

In one aspect of the present disclosure, a system including a hydraulic accumulator, a pressure sensor, a fluid source and a data processor can be provided. The hydraulic accumulator can include a first fluid chamber, a second fluid chamber filled with a compressible fluid, and a separator disposed therebetween. The hydraulic accumulator can have an associated pre-charge pressure. The pressure sensor can be configured to determine fluid pressure associated with the first fluid chamber. The fluid source can be connected with the first fluid chamber of the hydraulic accumulator. The data processor can be connected to the pressure sensor. The data processor is configured to determine a first rate of pressure change, a second rate of pressure change different than the first rate, and a transition pressure between the first and second rates. The data processor may determine an approximate pre-charge pressure of the hydraulic accumulator based on the transition pressure.

In another aspect, a method for determining an approximate pre-charge of a hydraulic accumulator. In one step, the method reduces a first fluid chamber of a hydraulic accumulator to a minimum volume state. The hydraulic accumulator has a second fluid chamber filled with a compressible fluid. In another step, the method provides a pressurized fluid to the first fluid chamber, wherein a pressure of the fluid in the first fluid chamber changes at a first rate and transitions to a second rate at a transition pressure. Subsequently, in yet another step, the method determines an approximate pre-charge pressure of the hydraulic accumulator based on the transition pressure.

Other features and aspects of this disclosure will be apparent from the following description and the accompanying drawings.

DETAILED DESCRIPTION

Figure 1:
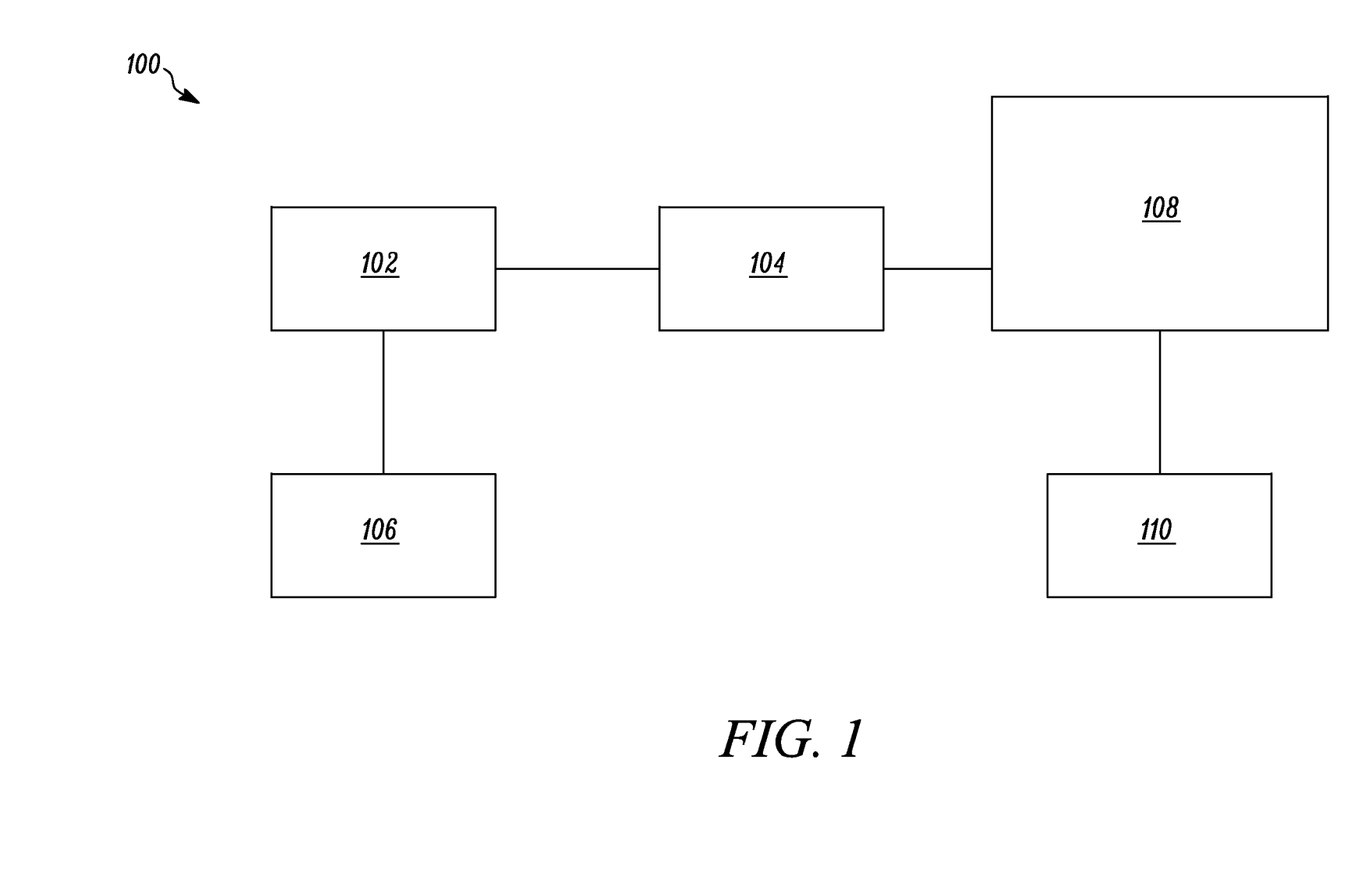
FIG. 1 is a block diagram of an exemplary system having a hydraulic accumulator and a data processor, according to one embodiment of the disclosure.
Figure 2:
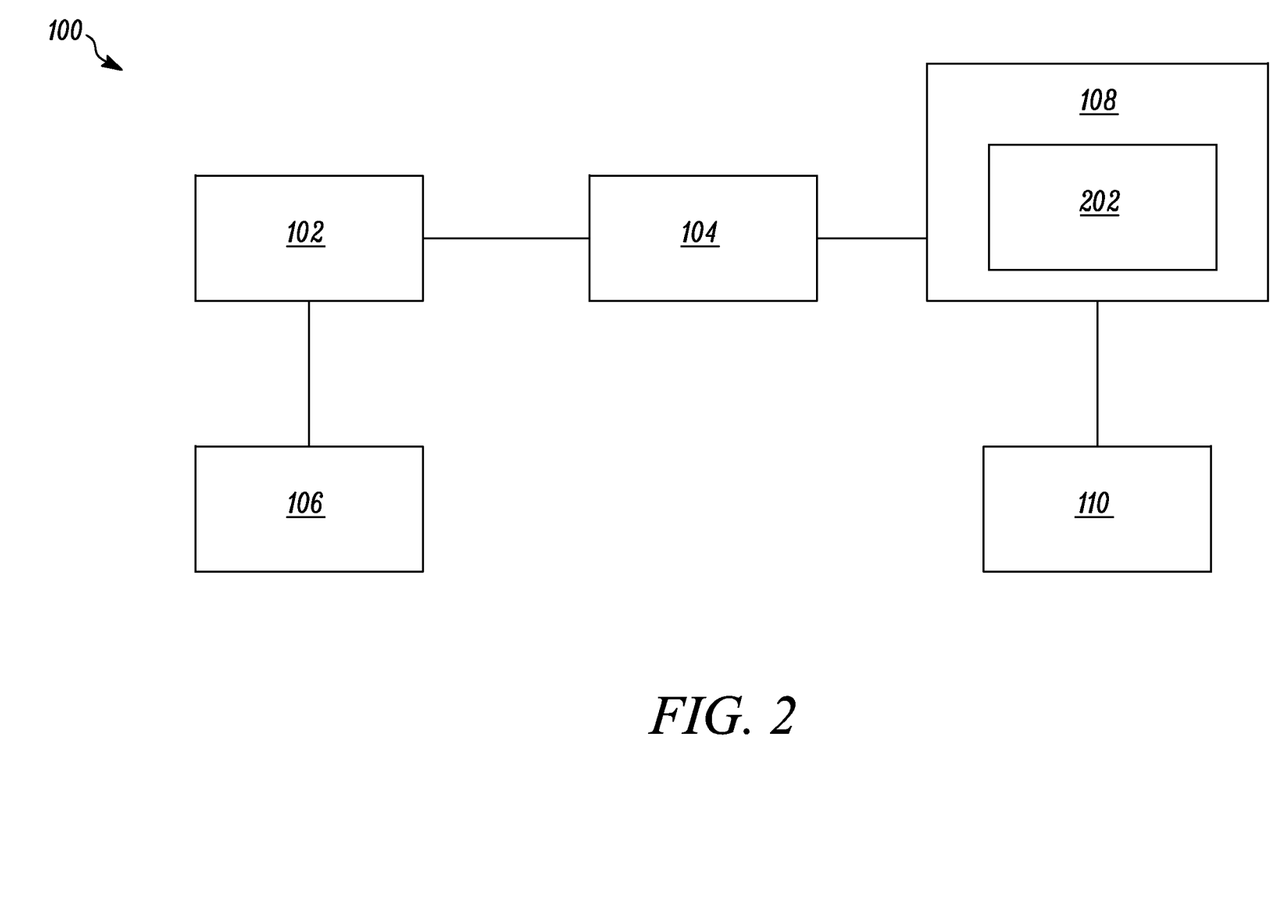
FIG. 2 is a block diagram of the system of FIG. 1 including a comparator.

FIGS. 1-2 illustrate an exemplary system 100 including a hydraulic accumulator 102, a pressure sensor 104, a fluid source 106 and a data processor 108, according to one embodiment of the present disclosure. The system 100 may be embodied in any machine such as excavators, wheel loaders, tractors and other machinery. The hydraulic accumulator 102 may be a piston-based accumulator or a bladder-based accumulator. One or more valves (not shown) may be associated with the system 100 to selectively control charging and discharging of the accumulator. For example, one or more valves may be open to permit charging and/or discharging of the accumulator, whereas one or more valves (same or different) may be closed to permit charging and/or discharging.

Figure 3:
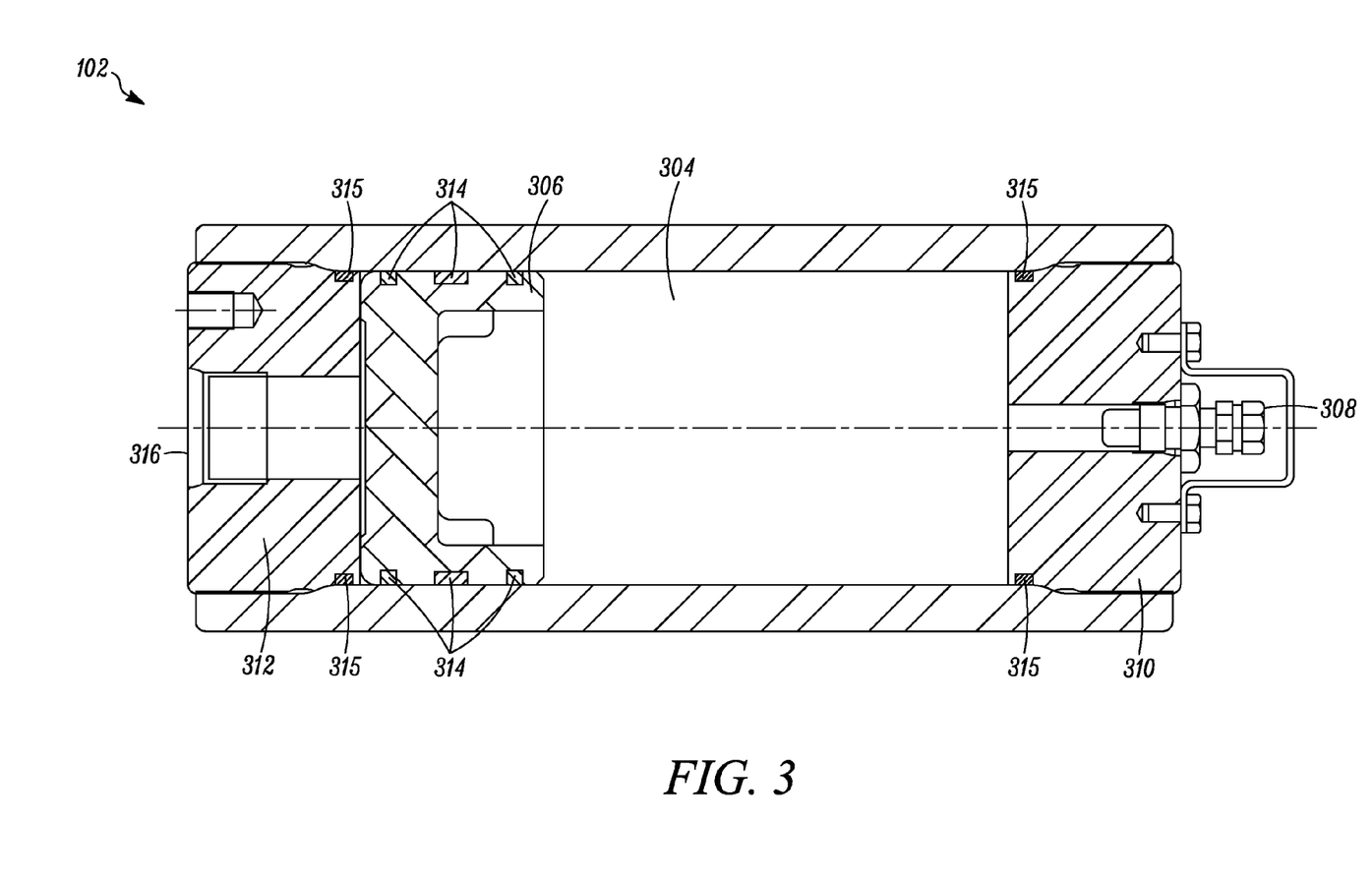
FIG. 3 is a diagrammatic view of the hydraulic accumulator in an minimum volume state.
Figure 4:
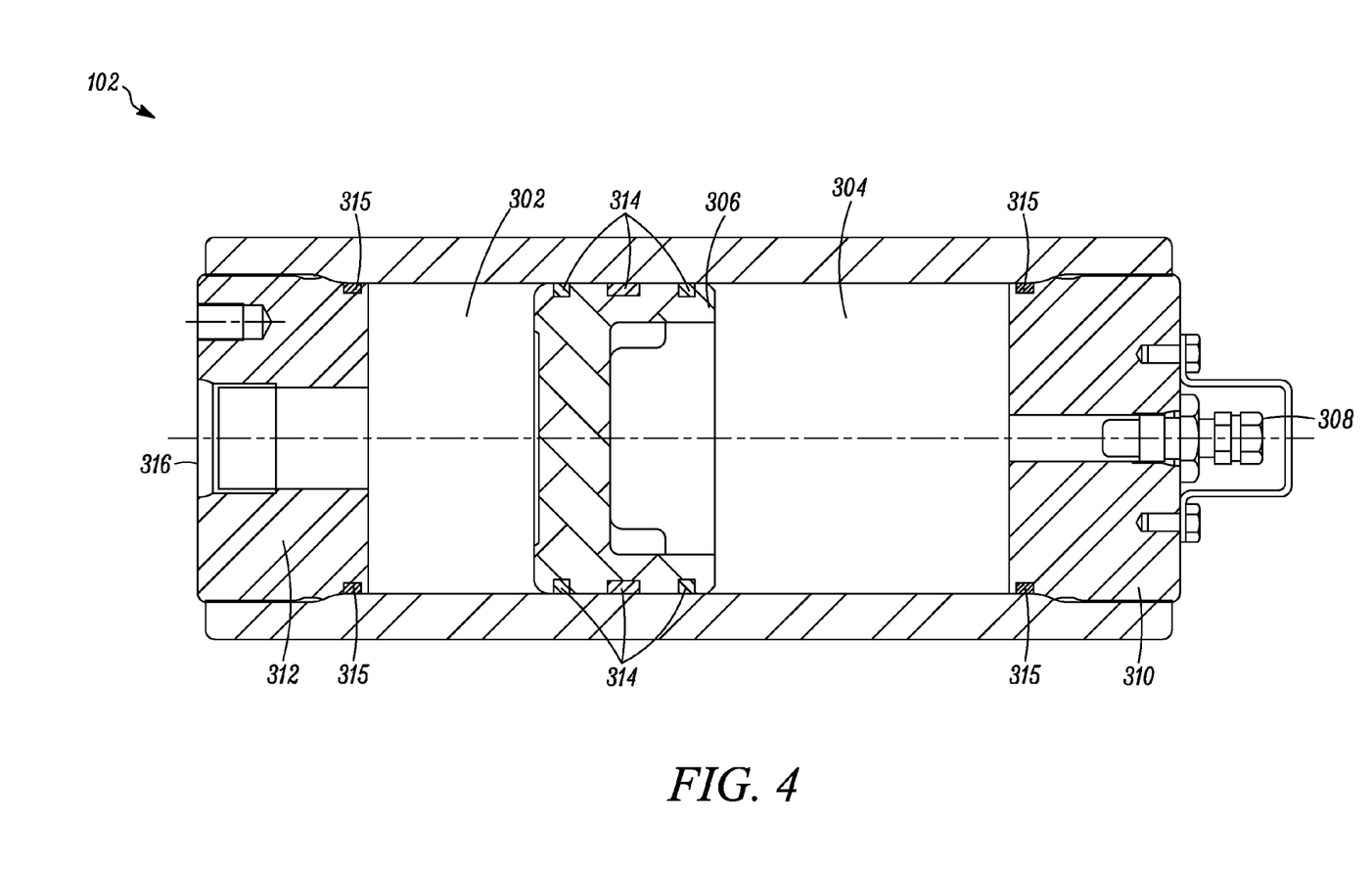
FIG. 4 is a diagrammatic view of the hydraulic accumulator at an intermediate state.

As shown in FIGS. 3-4, the hydraulic accumulator 102 may include a first fluid chamber 302, such as a working fluid or oil chamber, a second fluid chamber 304, such as a compressible fluid or gas chamber, and a separator 306 disposed between the chambers 302, 304. The first fluid chamber 302 may be configured to be filled with a first fluid. In one embodiment, the first fluid may include oil, lubricating fluid, or any other fluid associated with hydraulic machinery. The second fluid chamber 304 of the hydraulic accumulator 102 may be filled with a gas or any other compressible fluid via a gas valve 308. In one embodiment, the gas may be nitrogen. The separator 306 of the hydraulic accumulator 102 may be configured to separate the first fluid and second fluid chambers 302, 304 to keep the fluid contained therein substantially isolated from one another.

The hydraulic accumulator 102 may include a first end cap 310 associated with the second fluid chamber 304 and a second end cap 312 associated with the first fluid chamber 302. The separator 306 may be a piston having one or more seals 314 to reduce the risk of fluid from one chamber entering into the other chamber. The piston-like separator 306 is movable within the hydraulic accumulator 102 to reduce or increase the volume of the respective fluid chambers. Additional seals 315 may be provided in the first end cap 310 and the second end cap 312 of the hydraulic accumulator 102. Similarly, in case of a bladder-based accumulator, the separator 306 may be flexible membrane or an expandable separator being movable between an expanded configuration and a compressible configuration. The hydraulic accumulator 102 is sized to have a pre-charge pressure capacity to pressurize accumulated fluid within the first fluid chamber 302, e.g., for energy recovery, which is sequentially released from the first fluid chamber 302 at the pressure associated with the charged pressure of the second fluid chamber 304. The pre-charge pressure can be determined by the pressure capacity and difference between the first and second fluid chambers 302, 304.

To determine the pressure associated with the hydraulic accumulator 102, the pressure sensor 104 may be connected upstream or downstream of the first fluid chamber 302 of the hydraulic accumulator 102. The pressure sensor 104 may be configured to monitor and provide to the data processor 108 pressure readings of the fluid in the first fluid chamber 302 during charging and discharging of the hydraulic accumulator 102. In one embodiment, the pressure readings may either be provided continuously or after pre-determined intervals of time. In one example, the pressure sensor 104 can be a fluid or oil pressure sensor.

The first fluid chamber 302 of the hydraulic accumulator 102 can be connected to the fluid source 106, such as a fixed or variable displacement hydraulic pump. The first fluid chamber 302 of the hydraulic accumulator 102 is configured to receive and deliver fluid at a flow rate during accumulator charging and discharging modes, respectively. Parameters related to the pump such as flow rate, flow direction, and the like may vary. It should be understood that any other device which may regulate a flow of the fluid may also be utilized. One or more valves may be associated with the first fluid chamber 302 such that after discharging of the hydraulic accumulator 102, the valve is configured to prevent charging at specified periods.

As shown in FIGS. 1-2, the data processor 108 may be connected to the pressure sensor 104. The data processor 108 may be configured to receive and process the pressure readings taken by the pressure sensor 104. Moreover, the data processor 108 may determine an approximate pre-charge pressure of the hydraulic accumulator 102. Also, the data processor 108 may be configured to determine or estimate frictional forces associated with the separator 306 of the hydraulic accumulator 102. For example, determination of such frictional forces may be useful to determine the effectiveness of the seals 314 of a piston-based accumulator.

In one embodiment, as shown in FIG. 2, the data processor 108 may include a comparator 202 to diagnose a health of the hydraulic accumulator 102. The comparator 202 may compare at least one of the pre-charge pressure, the frictional forces with a pre-determined threshold range of pre-charge pressure and the frictional forces associated with the hydraulic accumulator 102 to diagnose the health of the hydraulic accumulator 102. In another embodiment, the comparator 202 may be an independent or separate module connected to the data processor 108 by known methods.

The data processor 108 and/or comparator 202 may include a processor unit, input and output ports, an electronic storage medium for executable programs and threshold values, random access memory, a data bus, and the like. The functionality of the data processor 108 and/or comparator 202 may further include other activities not described herein.

Also, the data processor 108 and/or the comparator 202 may retrieve or store the pressure readings in a database 110. The database 110 may store historical data values related to the threshold range of pre-charge pressure and frictional forces of the hydraulic accumulator 102. The database 110 may utilize data structures, index files, or any other data storage and retrieval technique, without any limitation. It should be understood that the exemplary system 100 may include other components not described herein.

Figure 5:
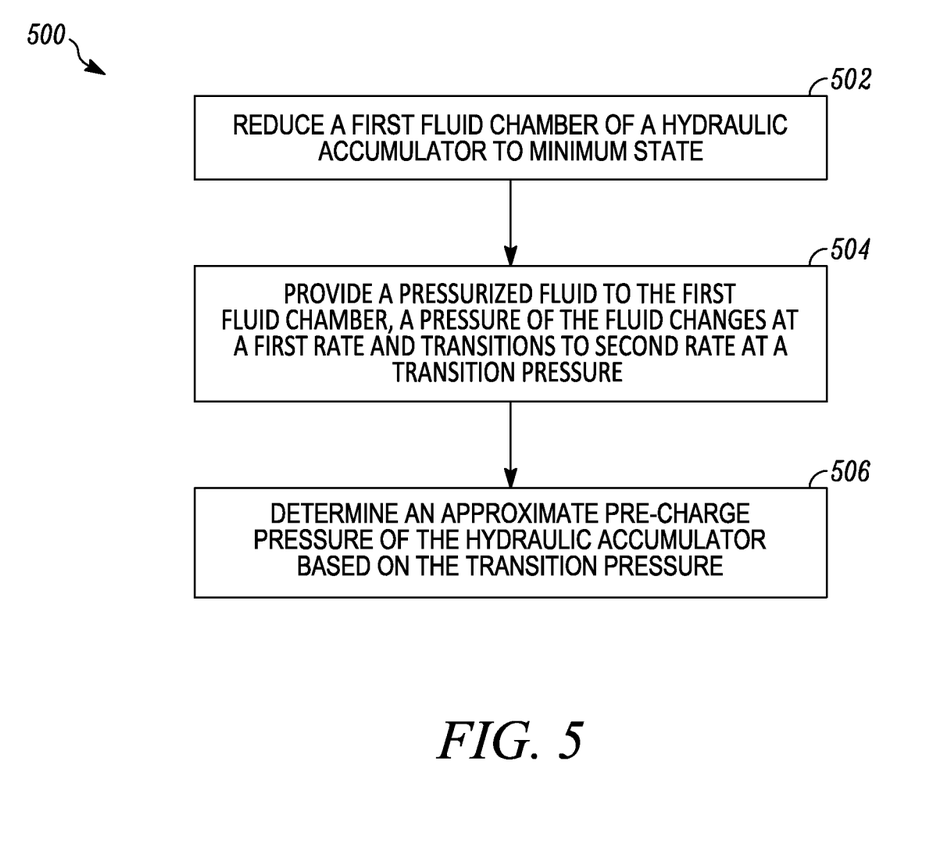
FIG. 5 is a process of determining an approximate pre-charge pressure of the hydraulic accumulator.
Figure 6:
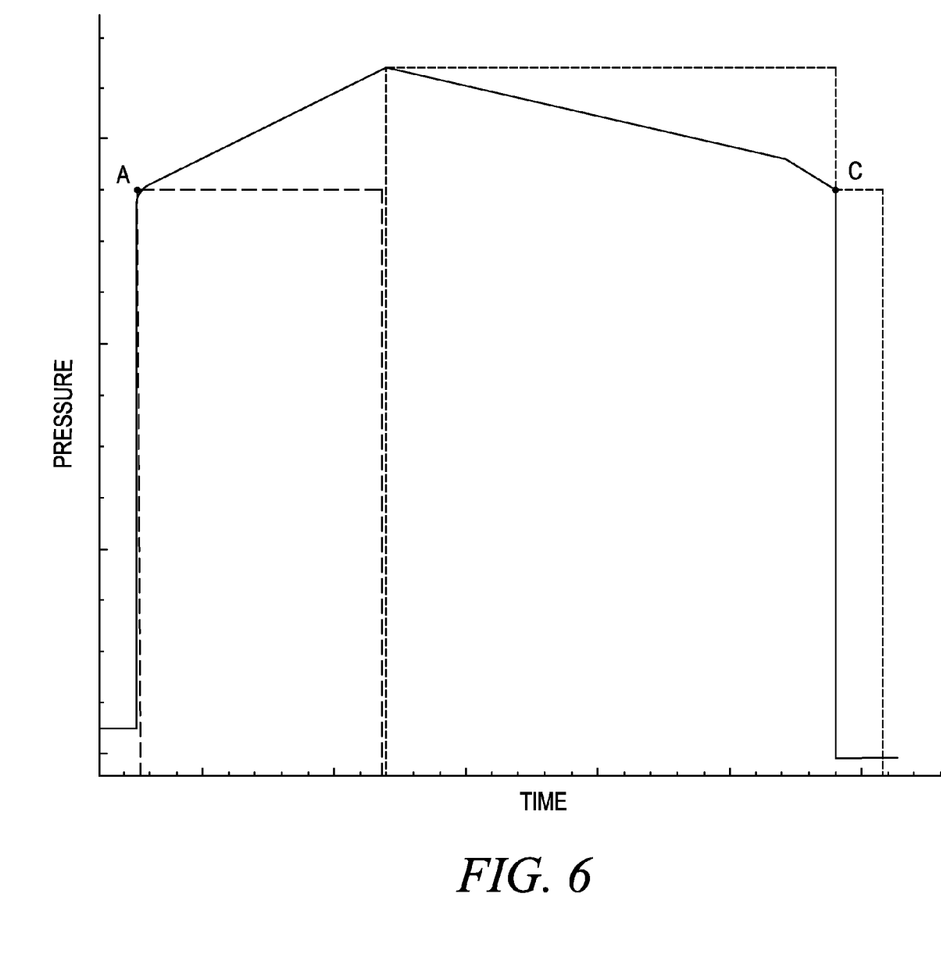
FIG. 6 is a graphical view of change in fluid pressure with respect to time during charging and discharging of the hydraulic accumulator.
Figure 7:
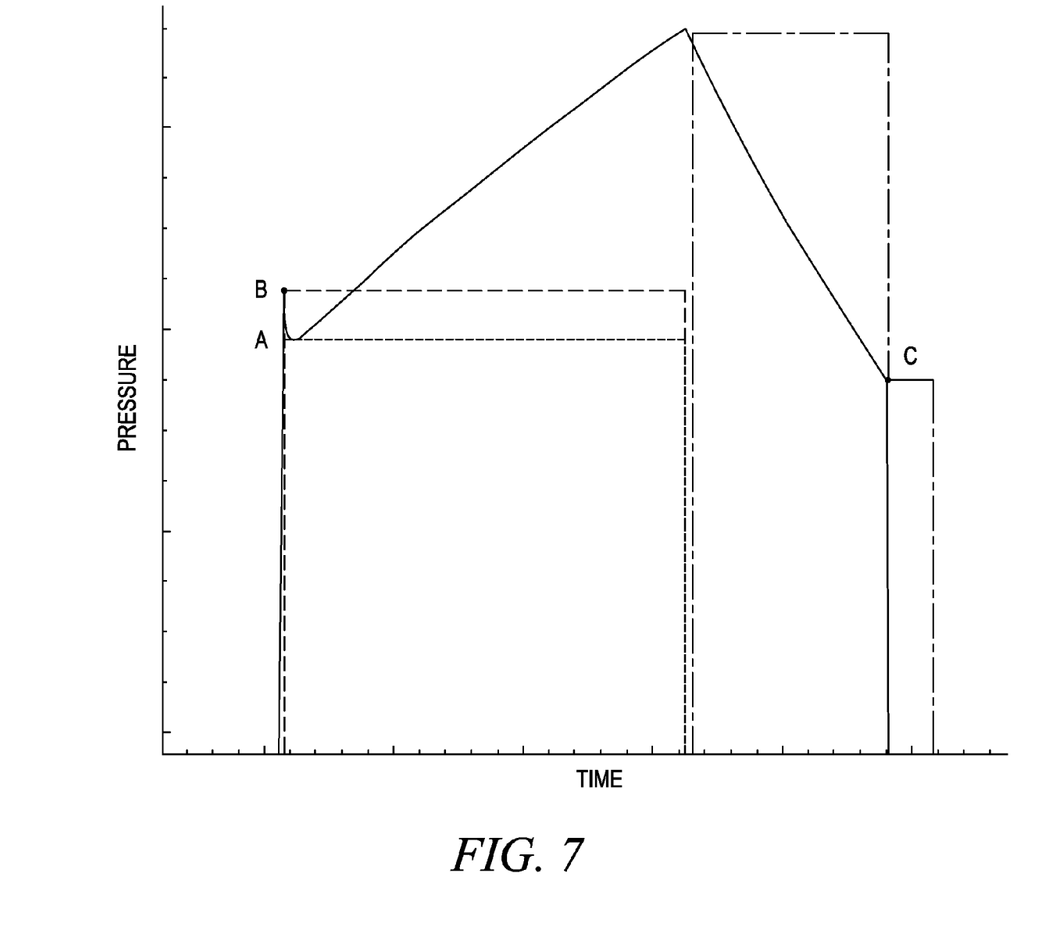
FIG. 7 is a graphical view of the change in fluid pressure with respect to time showing a peak pressure attained by the fluid pressure.

FIG. 5 illustrates a process for determining the pre-charge pressure of the hydraulic accumulator 102. FIGS. 6-7 are graphical views of the changes in the fluid pressure with respect to time, as monitored by the pressure sensor 104 which is connected to the hydraulic accumulator 102 during charging and discharging of the hydraulic accumulator 102.

Initially, the first fluid chamber 302 of the hydraulic accumulator 102 is connected to the fluid source 106. Fluid pressure may be driven to a minimum rate or zero such as, e.g., by withdrawing the fluid from the first fluid chamber 302 (that is, discharging fluid from the first fluid chamber 302) such that the hydraulic accumulator 102 is in an minimum volume state as shown in FIG. 3. In the piston-based accumulator, at the minimum volume state, the separator 306 of the hydraulic accumulator 102 may be in contact with walls of the first fluid chamber 302. Hence, as shown in step 502, the first fluid chamber 302 may be reduced to a minimum or zero volume state, while the second fluid chamber 304 may be at a maximum volume state. Here, the pressure readings of the fluid pressure of the first fluid chamber 302 at a minimum or zero volume may be monitored by the pressure sensor 104.

The pre-charge pressure of the hydraulic accumulator 102 is defined as the pressure of the inert gas or compressible fluid filled in the second fluid chamber 304 when the hydraulic accumulator 102 is in the minimum volume state. As seen the accompanied graphs, the fluid pressure recorded by the pressure sensor 104 at the minimum volume state is zero.

Subsequently, at step 504, the hydraulic accumulator 102 may be charged by providing the fluid to the first fluid chamber 302. FIG. 4 illustrates an intermediate state of the hydraulic accumulator 102 during the charging or discharging cycle. During charging, the fluid is provided to the first fluid chamber 302 by the fluid source 106, at the pre-determined flow rate via a port 316 located near the first fluid chamber 302. In one embodiment, the pump may be driven to minimum or low flow such as, e.g., about 30 lpm or less. Substantially faster rates can be more difficult to measure and control due to temperature increase and other factors. The pressure readings of the fluid pressure may be simultaneously monitored by the pressure sensor 104.

As the fluid is filled in the first fluid chamber 302, the separator 306 is pushed towards the second fluid chamber 304 of the hydraulic accumulator 102. For a certain interval of time, the pressure of the fluid may continue to remain zero or minimal until the frictional forces associated with the separator 306 are overcome and the separator 306 begins to move away from the second end cap 312.

When the separator 306 starts moving, the volume associated with the first fluid chamber 302 increases as the fluid fills into the first fluid chamber 302, causing a corresponding decrease in the volume associated with the compressible fluid filled in the second fluid chamber 304. At this time, the pressure of the fluid may change at a first rate and then transition to a second rate (see FIGS. 6-7). It may be observed that the first rate of change in the fluid pressure with time is greater than the second rate of change in the fluid pressure with time, as seen in the rapid change to the first rate and subsequent gradual transitioning to the second rate in the accompanied graphs.

Moreover, a reading of a first transition pressure may be monitored and recorded by the data processor 108. The first transition pressure of the fluid is the pressure at which the transitioning from the first to the second rate occurs. The first transition pressure is shown as Point A in the accompanied graphs. In one embodiment, the first transition pressure may be stored in the database 110 for retrieval. It should be noted that the associated pre-charge pressure of the hydraulic accumulator 102 may be the difference of a pressure of the fluid within the first fluid chamber 302 during the minimum volume state of the first fluid chamber 302 and the transition pressure.

In another embodiment, a peak pressure of the fluid (shown as Point B in FIG. 7) during the charging of the hydraulic accumulator 102, may be monitored and recorded by the data processor 108. The peak pressure of the fluid is greater than the recorded first transition pressure. The peak pressure may also be stored in the database 110.

The peak pressure of the fluid may be corresponding to the a required pressure of the fluid needed to initiate a change in the minimum volume state of the hydraulic accumulator 102, to overcome any frictional forces associated with moving the separator 306 towards the second fluid chamber 304. A person of ordinary skill in the art will appreciate that during charging of the hydraulic accumulator 102 from the minimum volume state, the fluid pressure may have to rise much higher to the peak pressure in order to overcome frictional forces and push the separator 306 towards the second fluid chamber 304. After the separator 306 begins to move, the fluid pressure may drop to the first transition pressure, as shown in FIG. 7.

The discharging of the hydraulic accumulator 102 may begin after a pre-determined pressure at the second rate is reached. Moreover, in one embodiment, the discharging may begin when a difference in pressure between the pre-determined pressure and the associated pre-charge pressure is 2 MPa. A person of ordinary skill in the art will appreciate that during charging of the hydraulic accumulator 102, a difference between the fluid pressure (associated with the first fluid chamber 302) and a gas pressure (associated with the second fluid chamber 304) may exist such that the fluid pressure may be slightly higher than the gas pressure at any instant.

The hydraulic accumulator 102 may be discharged by withdrawing the fluid from the first fluid chamber 302. The fluid may be withdrawn at a pre-determined flow rate via the port 316. In one embodiment, the pre-determined flow rate may be about 30 lpm or less. In another embodiment, the rate of withdrawal of the fluid during discharging may be the same as the rate of filling of the fluid during charging of the hydraulic accumulator 102.

During discharging of the hydraulic accumulator 102, based on the readings provided by the pressure sensor 104, the behavior of the fluid pressure may be as depicted in the FIGS. 6-7. The pressure of the fluid may change at a third rate and then transition to a fourth rate. As is clear from the FIGS. 6-7, the third rate of change in the fluid pressure with time is slower or gradual as compared to a greater or rapid fourth rate of change with time.

The data processor 108 may further monitor a second transition pressure (shown as Point C in FIGS. 6-7) at which the fluid pressure transitions from the third rate to the fourth rate. The second transition pressure may be stored in the database 110 by the data processor 108. It should be understood that during the discharging of the hydraulic accumulator 102, the difference between the fluid pressure and the gas pressure may be negligible. Also, after the hydraulic accumulator 102 is discharged, the fluid pressure may drop to zero while the gas pressure reaches the pre-charge pressure.

Subsequently, at step 506, the data processor 108 may determine an approximate pre-charge pressure of the hydraulic accumulator 102 based on the monitored transition pressure. In one embodiment, the determination may be based on the second transition pressure. In another embodiment, the determination of the approximate pre-charge pressure of the hydraulic accumulator 102 may be based on a co-relation of the first and second transition pressures.

The co-relation may include any mathematical function of the first and second transition pressure readings or the derivation of the approximate pre-charge pressure based on statistical analysis of the first and second transition pressure readings. In one embodiment, the data processor 108 may calculate an average of the first and second transition pressures to determine the approximate pre-charge pressure of the hydraulic accumulator 102.

It should be understood that the determined approximate pre-charge pressure may be substantially equivalent to the pressure of the hydraulic accumulator 102 at the minimum volume state. The rate of change of the gas pressure with time during charging and discharging of the hydraulic accumulator 102 may be proportional to the comparatively slower rate of change the fluid pressure with time recorded by the pressure sensor 104. The slower rates may be easier to read and control.

Additionally, the data processor 108 may determine the frictional forces associated with the separator 306, based on the monitored first, second, third and fourth rates. In yet another embodiment, the monitored first and second transition pressures, and the monitored first, second, third and fourth rates may be used to predict failure of the hydraulic accumulator 102.

Further, the data processor 108 may also determine the dynamic response of the hydraulic accumulator 102. The data processor 108 may retrieve from the database 110 and compare the peak pressure with the first transition pressure. Based on the comparison, the data processor 108 may determine the dynamic response of the hydraulic accumulator 102. In one embodiment, the difference in the peak pressure and the first transition pressure may be computed as the dynamic response of the hydraulic accumulator 102.

Further, the comparator 202 may facilitate diagnosis of the health of the hydraulic accumulator 102. The comparator 202 may retrieve from the database 110 one or more historical readings of the pre-charge pressure and/or the frictional forces associated with the hydraulic accumulator 102. In one embodiment, the historical readings may be readings determined by the data processor 108 or pre-determined threshold readings stored in the database 110. In another embodiment, the first transition pressure, peak pressure and the second transition pressure monitored may be compared to previous readings retrieved from the database 110, to determine a change in pre-charge pressure. For the piston based accumulator, the seal effectiveness may also be determined based on the comparison.

The comparator 202 may also be adapted to notify an operator if at least one of the determined pre-charge pressure and the frictional forces is not within the pre-determined threshold range. It should be understood that the notification may be provided to indicate that the determined approximate pre-charge pressure and/or the frictional forces of the hydraulic accumulator 102 may either be lower or higher than acceptable performance.

Moreover, the notification provided by the comparator 202 may be a visual feedback like an alert message, an audio feedback like a warning alarm, or any other type of feedback. Based on the notification, one or more remedial actions such as re-charging of the hydraulic accumulator 102, overhauling of the hydraulic accumulator 102 or replacement of the seals 314 in case of the piston-based accumulator may be performed.

INDUSTRIAL APPLICABILITY

On usage, the hydraulic accumulator 102 may lose the pre-charge pressure due to a variety of reasons. For example, reasons may be component failure such as, e.g., piston seal failure in the piston-based accumulator or bladder failure in the bladder-based accumulator. Further, gain in pre-charge pressure can be attributed by leakage of fluid into the second fluid chamber 304. Accordingly, if the pre-charge pressure is too high or too low, then the hydraulic accumulator 102 may require servicing or overhauling. Hence, the health of the hydraulic accumulator 102 may require to be checked once every few months or at least once a year after installation in a machine.

Typical solutions included connecting a pressure gauge and/or a modular kit to the gas valve 308 of the hydraulic accumulator 102. However, establishing this physical connection of the pressure gauge to the gas valve 308 is problematic when the hydraulic accumulator 102 is installed in the machine due to reduced accessibility. Also, sometimes manual analysis of the readings may be required in order to determine whether the hydraulic accumulator 102 is functioning properly. This may result in an increased cost associated with measuring of the pre-charge using these typical solutions. The systems and methods described herein may relate to an automated process for monitoring and diagnosing the health of the hydraulic accumulator 102, without requiring physical connection to the gas valve 308, i.e., without use of a gas gauge or sensor. The systems and methods described herein may determine and approximate pre-charge pressure and/or frictional values associated with the separator 306 of the hydraulic accumulator 102 to improve diagnosis of the accumulator health.

The diagnosis of the health and the determination of the approximate pre-charge pressure and/or the frictional values may be performed in real time by monitoring the pressure readings provided by the pressure sensor 104, and subsequently performing the necessary processing of the readings required for the determination.

The data processor 108 may determine the approximate pre-charge of the hydraulic accumulator 102 based on the monitored transition pressure. In one embodiment, the dynamic response of the hydraulic accumulator 102 may be determined based on the difference between the peak pressure and the first transition pressure.

Also, in another embodiment, the comparator 202 may determine if the approximate pre-charge pressure determined by the data processor 108 lies within the pre-determined threshold range. If the approximate pre-charge pressure is either too high or too low, that is, outside the range, then the operator may be suitably notified. Based on the notification, one or more remedial actions such as re-charging of the hydraulic accumulator 102 or replacement of the seal may be performed.

In case of the piston-based accumulator, the systems and methods described herein may determine the seal effectiveness of the separator 306. If the determined frictional values of the separator 306 lie within the pre-determined threshold range it may be indicative that the seals of the hydraulic accumulator 102 are in an acceptable condition and the seals 314 may be retained. For example, loss in pre-charge pressure can be due to component failure such as piston seal failure or bladder failure such that fluid leakage occurs from the second fluid chamber to the first fluid chamber. Gain in pre-charge pressure can be due to fluid leakage from the first fluid chamber into the second fluid chamber.

The frictional values may also be compared to the previous threshold range to determine if current values are acceptable or not. Relatively high frictional values may be indicative of a failure of the hydraulic accumulator 102 in the future. Hence, the disclosure may assist in the determining if the frictional values of the hydraulic accumulator 102 are higher than desired at early stage before failure.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A system comprising:
    a hydraulic accumulator having a first fluid chamber, a second fluid chamber filled with a compressible fluid, and a separator disposed therebetween, wherein the hydraulic accumulator is capable of an associated pre-charge pressure;
    a pressure sensor connected to the first fluid chamber;
    a fluid source to connect with the first fluid chamber; and
    a data processor connected to the pressure sensor, the data processor configured to:
        in response to fluid being provided to the first chamber of the hydraulic accumulator, determine a first rate of pressure change, a second rate of pressure change different than the first rate, and a first transition pressure between the first and second rates;
        in response to fluid being discharged from the first chamber of the hydraulic accumulator after the fluid reaches a pre-determined pressure at the second rate, determine a third rate of pressure change, a fourth rate of pressure change different from the third rate, and a second transition pressure between the third and fourth rates; and
        determine an approximate pre-charge pressure of the hydraulic accumulator based on the co-relation of the first and second transition pressures.

2. The system of claim 1, where in the pressure sensor is configured to provide a pressure reading of a fluid in the first fluid chamber to the data processor.

3. The system of claim 1, wherein the associated pre-charge pressure is the difference of a pressure of fluid within the first fluid chamber during a minimum volume state of the first fluid chamber and at least one of the first and second transition pressures.

4. The system of claim 1, wherein the fluid source includes a pump configured to provide a pressurized fluid to the first fluid chamber.

5. The system of claim 1, wherein the data processor is further configured to monitor a rate of change of pressure, with respect to time, of the fluid to determine frictional forces associated with the separator of the hydraulic accumulator.

6. The system of claim 1, wherein the hydraulic accumulator is a piston-based accumulator and the separator is a piston having one or more seals.

7. The system of claim 1, wherein the hydraulic accumulator is a bladder-based accumulator and the separator is a rubber separator.

8. A method comprising:
    reducing a first fluid chamber of a hydraulic accumulator to a minimum volume state;
    providing a pressurized fluid to the first fluid chamber, wherein a pressure of the fluid in the first fluid chamber changes at a first rate and transitions to a second rate at a first transition pressure;
    discharging the fluid from the first fluid chamber after the fluid reaches a pre-determined pressure at the second rate, wherein a pressure of the fluid in the first fluid chamber changes at a third rate and transitions to a fourth rate at a second transition pressure; and determining an approximate pre-charge pressure of the hydraulic accumulator based on a co-relation of the first and second transition pressures.

9. The method of claim 8 further comprising monitoring the first rate, the second rate, the third rate, the fourth rate, and the first and second transition pressures; and determining frictional forces associated with the hydraulic accumulator based on the first, second, third and fourth rates.

10. The method of claim 8, wherein the first rate is greater than the second rate.

11. The method of claim 10, wherein the fourth rate is greater than the third rate.

12. The method of claim 8, wherein the determining an approximate pre-charge pressure step comprises calculating an average of the first and second transition pressures.

13. The method of claim 8 further comprising monitoring a peak pressure of the fluid between the change of pressure rates of the second and third rates, wherein the peak pressure of the fluid is greater than the first transition pressure.

14. The method of claim 13, wherein the peak pressure of the fluid is corresponding to a required pressure of the fluid to initiate a change in the minimum volume state of the hydraulic accumulator.

15. The method of claim 14 further comprising:
comparing the peak pressure with the first transition pressure to determine a dynamic response of the hydraulic accumulator based on the comparison.

16. The method of claim 8, wherein the minimum volume state of the hydraulic accumulator is associated with a minimum volume state of the first fluid chamber and a maximum volume state in the second fluid chamber of the hydraulic accumulator.

17. A computer based system comprising:
a communication interface communicating with a memory;
the memory configured to communicate with a processor; and
the processor, in response to executing a computer program, performs operations comprising:
reducing a first fluid chamber of a hydraulic accumulator to a minimum volume state;
providing a pressurized fluid to the first fluid chamber, wherein a pressure of the fluid in the first fluid chamber changes at a first rate and transitions to a second rate at a first transition pressure;
discharging the fluid from the first fluid chamber after the fluid reaches a pre-determined pressure at the second rate, wherein a pressure of the fluid in the first fluid chamber changes at a third rate and transitions to a fourth rate at a second transition pressure; and
determining an approximate pre-charge pressure of the hydraulic accumulator based on a co-relation of the first and second transition pressures.

18. The computer based system of claim 17, further comprising:
monitoring the first rate, the second rate, the third rate, the fourth rate, and the first and second transition pressures; and
determining frictional forces associated with the hydraulic accumulator based on the first, second, third and fourth rates.

19. The computer based system of claim 17 further comprising determining an approximate pre-charge pressure comprises calculating an average of the first and second transition pressures.

20. The computer based system of claim 17 further comprising monitoring a peak pressure of the fluid between the change of pressure rates of the second and third rates, wherein the peak pressure of the fluid is greater than the first transition pressure.

* * * * *